(12) United States Patent
Bass (10) Patent No.: US 6,587,579 B1
(45) Date of Patent: Jul. 1, 2003

(54) FEATURE QUALITY IN ARRAY FABRICATION

(75) Inventor: Jay K. Bass, Mountain View, CA (US)

(73) Assignee: Agilent Technologies Inc., Palo Alto, CA (US)

( * ) Notice: Subject to any disclaimer, the term of this patent is extended or adjusted under 35 U.S.C. 154(b) by 0 days.

(21) Appl. No.: 09/491,527

(22) Filed: Jan. 26, 2000

(51) Int. Cl.[7] .......................... G06K 9/00; G06F 19/00; G01N 33/48; G01N 33/50
(52) U.S. Cl. .............................. 382/141; 435/6; 702/19; 702/20
(58) Field of Search .................... 702/19, 20; 435/6; 436/518; 356/364, 369; 382/141

(56) References Cited

U.S. PATENT DOCUMENTS

| | | |
|---|---|---|
| 4,067,019 A | 1/1978 | Fleischer et al. |
| 4,128,841 A | 12/1978 | Brown et al. |
| 4,323,905 A | 4/1982 | Reitberger et al. |
| 4,675,696 A | 6/1987 | Suzuki |
| 4,872,028 A | 10/1989 | Lloyd |
| 5,124,720 A | 6/1992 | Schantz |
| 5,449,754 A | 9/1995 | Nishioka |
| 5,508,178 A | 4/1996 | Rose et al. |
| 5,508,200 A | 4/1996 | Tiffany et al. |
| 5,554,339 A | 9/1996 | Cozzette et al. |
| 5,578,832 A | 11/1996 | Trulson et al. |
| 5,581,487 A | 12/1996 | Kelly et al. |
| 5,585,639 A | 12/1996 | Dorsel et al. |
| 5,601,980 A | 2/1997 | Gordon et al. |
| 5,631,734 A | 5/1997 | Stern et al. |
| 5,658,802 A | 8/1997 | Hayes et al. |
| 5,721,435 A | 2/1998 | Troll |
| 5,744,305 A | 4/1998 | Fodor et al. |
| 5,760,951 A | 6/1998 | Dixon et al. |
| 5,763,870 A | 6/1998 | Sadler et al. |
| 5,800,992 A | 9/1998 | Fodor et al. |
| 5,801,970 A | 9/1998 | Rowland et al. |
| 5,807,522 A | 9/1998 | Brown et al. |
| 5,812,272 A | 9/1998 | King et al. |
| 5,815,593 A | 9/1998 | Shaum et al. |
| 5,825,483 A | 10/1998 | Michael et al. |
| 5,834,758 A | 11/1998 | Trulson et al. |
| 5,837,475 A | 11/1998 | Dorsel et al. |
| 5,843,655 A | 12/1998 | McGall |
| 5,856,174 A | 1/1999 | Lipshutz et al. |
| 5,861,242 A | 1/1999 | Chee et al. |
| 5,981,733 A | 11/1999 | Gamble et al. |
| 5,982,534 A | 11/1999 | Pinkel et al. |
| 5,984,470 A | 11/1999 | Sakino et al. |
| 6,001,309 A | 12/1999 | Gamble et al. |
| 6,024,925 A | 2/2000 | Little et al. |
| 6,045,996 A | 4/2000 | Cronin et al. |
| 6,140,044 A | 10/2000 | Besemer et al. |
| 6,232,072 B1 * | 5/2001 | Fisher ............................ 435/6 |
| 6,238,862 B1 * | 5/2001 | McGall et al. .................. 435/6 |
| 6,399,396 B1 * | 6/2002 | Bass ........................... 436/180 |
| 6,406,851 B1 * | 6/2002 | Bass ............................. 435/6 |
| 6,420,180 B1 * | 7/2002 | Bass ........................... 436/43 |

FOREIGN PATENT DOCUMENTS

| | | |
|---|---|---|
| EP | 0 334 546 | 9/1998 |
| GB | 2 355 716 | 5/2001 |
| WO | WO 93/17325 | 9/1993 |
| WO | WO 95/25116 | 9/1995 |
| WO | WO 98/41531 | 9/1998 |
| WO | WO 99/05308 | 2/1999 |
| WO | WO 00/34523 | 6/2000 |
| WO | WO 00/60425 | 10/2000 |

OTHER PUBLICATIONS

Chen, Y. et al., "Ratio–Based Decisions and the Quantitative Analysis of cDNA Microarray Images", Journal of Biomedical Optics, vol. 2, No. 4, 1997, pp. 364–374.

European Search Report and Annex to the European Search Report dated Oct. 31, 2002.

Budach et al., "Planar Waveguides as High–Performance Sensing Platforms for Fluorescence–Based Multiplexed Oligonucleotide Hybridization Assay", Analytical Chemistry, Vo.. 71, pp.3347–3355, 1999.

Marshall, A. and Hodgson, J., "DNA Chips: An Array of Possibilities", Nature Biotechnology, vol. 16, pp. 27–31, Jan. 1998.

Instruction Page, "Programmable Error Connection PKE 80", RSF Electronik, Rancho Cordova, CA, (undated).

"BioChip Arrayer: Automated DNA Microarray Fabrication", http://www.packardinst.com/prod_serv/biochiparrayer.htm, Packard Instrument Company, 1999, 3 pp., date downloaded—Oct. 13, 1999.

"Press Release: New Options Optimize Arraying Technology", http://www.packardinst.com/pr/pr899–2.htm, Packard Instrument Company, Aug. 1, 1999, 2 pp., date downloaded—Oct. 13, 1999.

* cited by examiner

*Primary Examiner*—Marianne P. Allen
(74) *Attorney, Agent, or Firm*—Gordon M. Stewart

(57) ABSTRACT

A method, and apparatus and computer program products for executing the method. The method includes obtaining a set of multiple images of a target feature location on an array of multiple features, each image of the set representing the target feature location following deposition of a corresponding sub-set of multiple droplets for that feature. An overlay composite may be generated from the image set. The overlay composite may be used as a quality control tool, or in interrogating the array or processing results of the interrogation.

6 Claims, 3 Drawing Sheets

FEATURE QUALITY IN ARRAY FABRICATION

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers (such as from synthesis or natural sources) onto a substrate, or by in situ synthesis methods. Methods of depositing obtained biopolymers include loading then touching a pin or capillary to a surface, such as described in U.S. Pat. No. 5,807,522 or deposition by firing from a pulse jet such as an inkjet head, such as described in PCT publications WO 95/25116 and WO 98/41531, and elsewhere. For in situ fabrication methods, multiple different reagent droplets are deposited at a given target location in order to form the final feature (hence a probe of the feature is synthesized on the array stubstrate). The in situ fabrication methods include those described in U.S. Pat. No. 5,449,754 for synthesizing peptide arrays, and described in WO 98/41531 and the references cited therein for polynucleotides. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence is as follows: (a) coupling a selected nucleoside through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner.

The foregoing chemistry of the synthesis of polynucleotides is described in detail, for example, in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, 5,869, 643, EP 0294196, and elsewhere. The phosphoramidite and phosphite triester approaches are most broadly used, but other approaches include the phosphodiester approach, the phosphotriester approach and the H-phosphonate approach. The substrates are typically functionalized to bond to the first deposited monomer. Suitable techniques for functionalizing substrates with such linking moieties are described, for example, in Southern, E. M., Maskos, U. and Elder, J. K., Genomics, 13, 1007–1017, 1992.

In the case of array fabrication, different monomers may be deposited at different addresses on the substrate during any one iteration so that the different features of the completed array will have different desired biopolymer sequences. One or more intermediate further steps may be required in each iteration, such as the conventional oxidation and washing steps in the case of in situ fabrication of polynucleotide arrays.

In array fabrication, the quantities of polynucleotide available are usually very small and expensive. Additionally, sample quantities available for testing are usually also very small and it is therefore desirable to simultaneously test the same sample against a large number of different probes on an array. These conditions require use of arrays with large numbers of very small, closely spaced features. It is important in such arrays that features actually be present, that they are put down accurately in the desired target pattern, are of the correct size, and that the DNA is uniformly coated within the feature. If any of these conditions are not met within a reasonable tolerance, and the array user is not aware of deviations outside such tolerance, the results obtained from a given array may be unreliable and misleading. This of course can have serious consequences to diagnostic, screening, gene expression analysis or other purposes for which the array is being used. However, in any system used to fabricate arrays with the required small features, there is inevitably some degree of error, either fixed (and hence repeated) and/or random. The present invention realizes that in the special case of in situ fabrication method or any other method requiring deposition of multiple droplets at a target feature location, drop deposition errors from cycle to cycle may be different and are cumulative in determining errors in the finally formed features.

It would be desirable then to provide a means by which errors in features resulting during an in situ or any array fabrication method requiring multiple droplet deposition for a target feature location, can be readily determined.

SUMMARY OF THE INVENTION

The present invention further realizes that in array fabrication using the in situ method or any method using multiple drop deposition for a target feature location, the final error in a feature is a sum of errors during respective droplet depositions, and that such individual droplet errors may vary during each cycle at a given feature. Such errors may either be fixed or random. For example, in the fabrication of a polynucleotide array using phosphoramidite chemistry, different drop dispensers (such as pulse jets which eject drops drops toward a surface) may be provided to deposit different phosphoramidite droplets. Each nozzle may have its own inherent fixed drop dispensing error (such as error in drop dispenser position within a head, droplet size, or direction of drop). Also, the positioning system may have fixed inherent errors. Further, random errors can occur which are different during the dispensing of any one droplet. For example, air currents may vary during different droplet dispensing steps, or ambient temperature variations may cause expansion/contraction in dispensing apparatus components which affects absolute and/or relative positions of dispensed droplets. Thus, an error in the final feature may be a sum of errors from individual drop deposition at each feature. The present invention provides a means of tracking such individual droplet deposition error for a feature and using such multiple drop deposition error for that feature to determine an overall feature error.

In one aspect, the present invention provides a method which includes obtaining a set of multiple images of a target feature location on an array of multiple features. Each image of the set represents the target feature location following deposition of a corresponding sub-set of multiple droplets for that feature. An overlay composite is generated from the image set. Note that the processing for this can be done as each image of a set is obtained or after all images of a set are obtained. By an "overlay composite" in this context is referenced that information from at least one same location on the set of images is combined or compared using some function (for example, logical AND or some other operation). The same location may be, for example, all of the target feature location plus some predetermined area around that location, or just some point or portion of the foregoing. A particular overlay composite comprises a region of overlap of the multiple droplets. One or more feature characteristics (for example, the extent, size, shape or location of overlap of deposited droplets) may be provided by the overlay composite. Typically, since an array will usually contain many features and it will be desirable to determine feature characteristics of multiple such features (and perhaps all of them), the method may be used by obtaining multiple image sets of respective multiple target feature locations. In this case each image set represents a corresponding target feature location with each image of the set representing the location following deposition of a corresponding sub-set of multiple droplets for that feature. An overlay composite may then be generated from each of the image sets.

The above aspect may be used in the fabrication of arrays, or by an end user of the array or elsewhere. When the method is used in fabrication, it will also typically include depositing multiple reagent droplets for each of multiple target feature locations so as to form the array of features, and obtaining the image sets during such fabrication. In the fabrication, the image set is typically obtained by capturing an image of each target feature location following deposition of a corresponding drop sub-set (for example, from multiple captured images each of which simultaneously includes multiple target feature locations following a cycle of droplet depositions at those locations). When the above aspect is used by an end user or elsewhere, the image sets may be obtained by other means (such as from a portable data storage medium associated with the array and carrying the image sets as digital data, or from communication with a remote array fabricator).

The overlay composite can be used for any of a number of purposes. For example, the overlay composite may also be used by the fabricator as a quality control tool such as by rejecting arrays with one or more feature characteristics which do not meet predetermined requirements, and/or by altering the deposition of additional droplets for the feature, or of droplets for other features on the same or another array. Such rejecting or altering may be based at least in part on the overlay composite. Additionally, the overlay composite may be forwarded to a remote user of the array for use by them in interrogating the array or processing data resulting from the interrogation. Typically, the remote user will expose the array to a sample, interrogate the array following the exposure and optionally process the results of the evaluation (such as for evaluating the sample composition, for example, for the presence of a component). The interrogation or processing may be based at least in part on the overlay composite. However, in an alternative aspect of the present invention, rather than (or in addition to) forwarding the composite overlay to the remote user, the image sets themselves may be stored on a storage medium and forwarded to the remote user (such as by hard copy or on a portable digital data storage medium, or by communication). Any forwarding to the remote user may be, for example, be by hard copy or portable digital data storage medium carrying the required information, or by communication over a suitable communication channel.

The present invention also provides an apparatus for fabricating an array in accordance with any of the methods of the invention. The apparatus may include a drop deposition system to deposit multiple reagent droplets for each of multiple target feature locations so as to form the array of features. An image capture system provides the one or more sets of multiple images previously referenced. The apparatus may further include either a processor which generates an overlay composite from the image set and optionally performs any the processing previously described, or a storage medium onto which the image set or an overlay composite of them are stored, or both. Optionally, a communication module is present to communicate an image set or overlay composite to a remote location.

The present invention further provides a computer readable storage medium carrying program code which can be used with an apparatus of the present invention, to cause it to execute the steps of a method of the present invention.

The various aspects of the present invention can provide any one or more of the following and/or other useful benefits. For example, individual droplet deposition errors during an in situ or any array fabrication method requiring multiple droplet deposition for a target feature location, can be readily determined and tracked, and resultant feature errors determined from those individual droplet errors. Such results can be used as quality control tools during array fabrication and/or forwarded to a remote location for use in interrogating or processing interrogation results from the corresponding array.

DETAILED DESCRIPTION OF EMBODIMENTS OF THE INVENTION

In the present application, unless a contrary intention appears, the following terms refer to the indicated characteristics. A "biopolymer" is a polymer of one or more types of repeating units. Biopolymers are typically found in biological systems and particularly include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948, 902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one or two dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and some indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information over a suitable communication channel (for example, a private or public network). "Forwarding" an item refers to any means of getting that item from one location to the next, whether by physically transporting that item and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. "Fluid" is used herein to reference a liquid. An "image" in relation to a target feature location following droplet deposition, refers to data on shape, size or position of the whole or part of the droplet (in liquid form or after drying), regardless of how such data was obtained (for example by capturing with a camera, or by scanning with a laser beam, or by some other means). A "set" or a "sub-set" may have one or more members (for example, one or more droplets). Reference to a singular item, includes the possibility that there are plural of the same items present. All patents and other cited references are incorporated into this application by reference.

Figure 1:
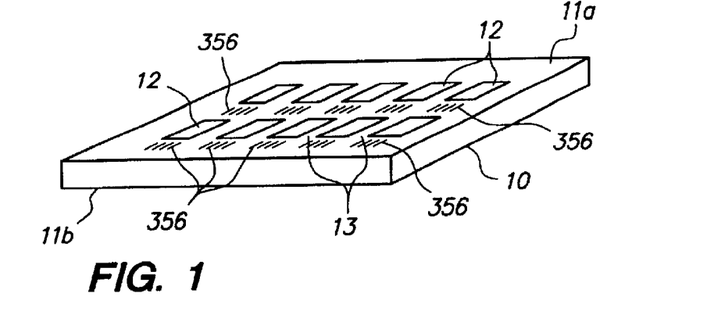
FIG. 1 illustrates a substrate carrying multiple arrays, such as may be fabricated by methods of the present invention.
Figure 2:
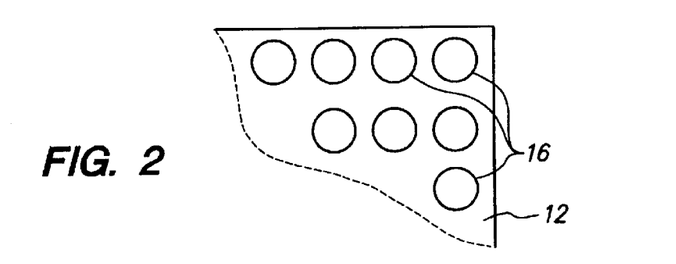
FIG. 2 is an enlarged view of a portion of FIG. 1 showing multiple ideal spots or features.
Figure 3:
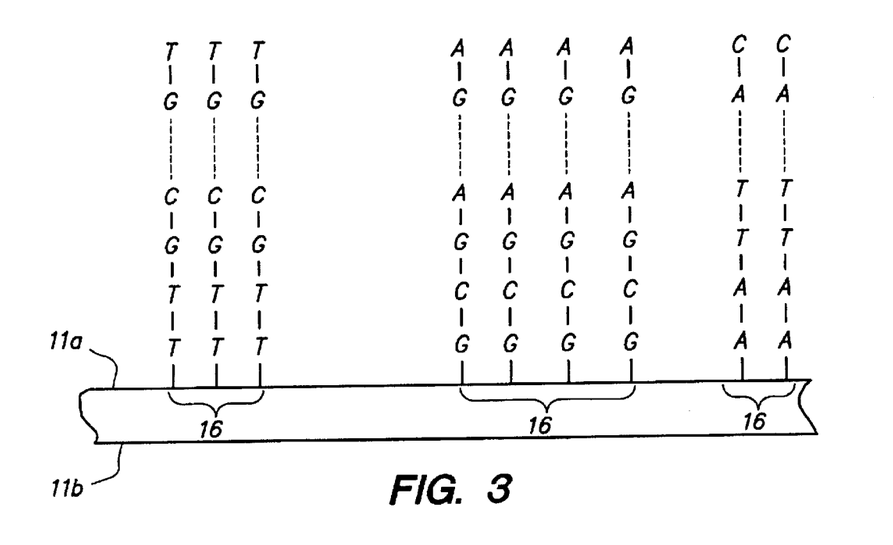
FIG. 3 is an enlarged illustration of a portion of the substrate in FIG. 2.

Referring first to FIGS. 1–3, typically methods and apparatus of the present invention generate or use a contiguous planar substrate 10 carrying one or more arrays 12 disposed across a front surface 11*a* of substrate 10 and separated by inter-array areas 13. A back side 11*b* of substrate 10 does not carry any arrays 12. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). Each array 12 has associated with it a unique identification in the form of a bar code 356. While ten arrays 12 are shown in FIG. 1 and the different embodiments described below may use substrates with particular numbers of arrays, it will be understood that substrate 10 and the embodiments to be used with it, may use any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some or all could be the same. In the embodiment illustrated, there are interfeature areas 17 between features, which do not carry any polynucleotide. It will be appreciated though, that the interfeature areas 17 could be of various sizes and configurations. It will be appreciated that there need not be any space separating arrays 12 from one another, nor features 16 within an array from one another. However, in the case where arrays 12 are formed by the conventional in situ method as described above, by depositing for each feature a droplet of reagent in each step such as by using a pulse jet such as an inkjet type head, such interfeature areas 17 will typically be present. Each feature carries a predetermined polynucleotide (which includes the possibility of mixtures of polynucleotides). As per usual, A, C, G, T represent the usual nucleotides. It will be understood that there is usually a linker molecule (not shown) of any known types between the front surface 11*a* and the first nucleotide.

Figure 4:
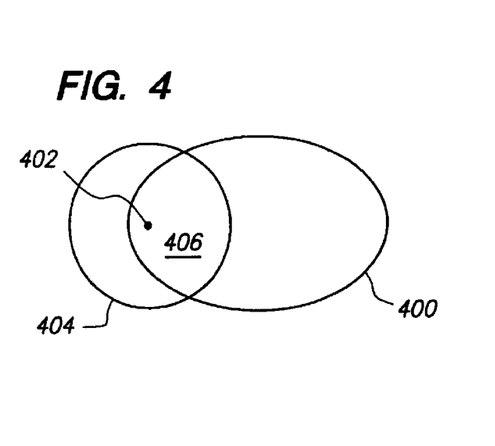
FIGS. 4 and 5 illustrate examples of formation of overlay composites for less than ideal features.
Figure 5:
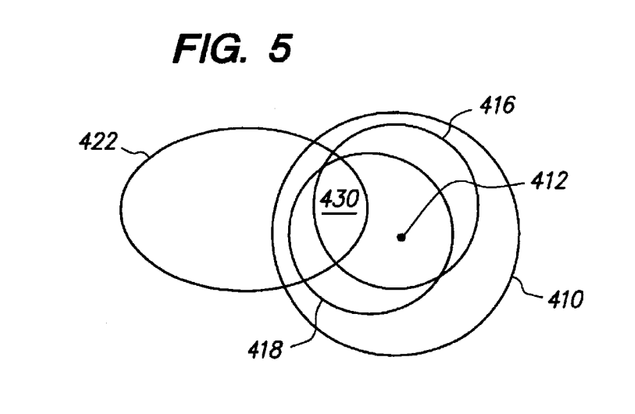

FIGS. 2 and 3 illustrate ideal features where the actual features formed are the same as the target (or "aim") features, with each feature 16 being uniform in shape, size and composition, and the features being regularly spaced. Such an array when fabricated by the in situ method, would require all reagent droplets for each feature to be uniform in shape and accurately deposited at the target feature location. In practice, such an ideal result is difficult to obtain due to both the fixed and random errors such as those discussed above. FIG. 4 shows images of two phosphoramidite droplets deposited in different cycles, for a particular feature (that is FIG. 4 shows an image set for that feature), and illustrates a less than ideal result. FIG. 5 similarly illustrates an image set for another feature of five phosphoramidite droplets with a less than ideal actual feature being formed (reference to the shape of the deposited droplets will, in the following discussion, refer to dried droplet shape). The droplet errors illustrated in FIGS. 4 and 5 have been somewhat exaggerated for the purpose of clarity. For the discussion which follows, it will be assumed that each "sub-set" of droplets after which an image is captured, consists of only one set. However, in practice each such sub-set will typically consist of multiple droplets of the same composition. In FIG. 4, a nucleoside phosphoramidite reagent droplet 404 (such droplets being often referenced simply as "phosphoramidite" droplets) of circular shape has been deposited in one cycle with its center exactly at the center 402 of the target feature location. However, another phosphoramidite droplet 400 deposited in a subsequent or earlier cycle has an elliptical shape due to fixed or random errors, and has its center mis-aligned with target feature center 402. If the target feature was only to be formed from the foregoing two phosphoramidites, the actual feature having the desired nucleotide sequence would only consist of overlap region 406 (which is the intersection of the droplets, or logical AND of them), which is neither of the target circular shape nor on the target feature center. Similarly, in FIG. 5 where five phosphoramidites droplets 410, 416, 418, 422 are deposited in different cycles for a target feature, one droplet 410 is centered on target feature center 412 and is correctly shaped (circular) but is too large, while droplets 416, 418 have the target shape and size but are off the center 412, and droplet 422 is both of the wrong shape, size and position. In this case, the resulting actual feature 430 of five nucleotides in length, would again be the overlap (or logical AND) of the droplets. Note that actual feature 430 is of incorrect shape and size, and does not even overlap the target center 412.

Thus, as illustrated in FIGS. 4 and 5, when an image of each of the deposited reagent droplets in the multi-cycle in situ synthesis are obtained (such as by obtaining an image of each entire droplet), formation of an overlay composite can provide information on one or more characteristics of an actual feature. In the particular cases described in connection with FIGS. 4 and 5, a logical AND operation is applied to the set of such images for a given feature to provide the overlap region characteristics (such as size, shape and location) and hence the characteristics of the actual feature. As is apparent from FIGS. 4 and 5, overlay composites formed from a logical AND operation, automatically provides an evaluation of feature characteristics.

Figure 6:
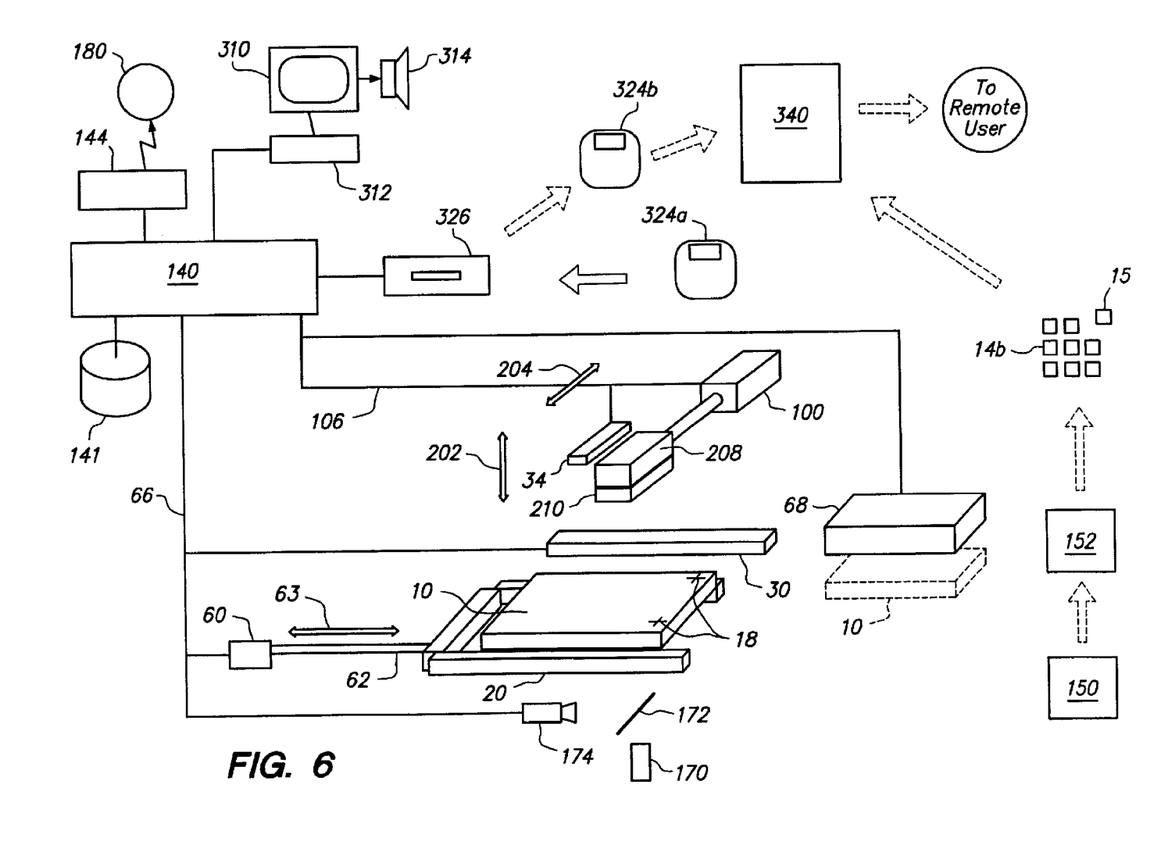
FIG. 6 is a schematic diagram of a fabrication apparatus and method of the present invention.

Referring now to FIG. 6, an apparatus of the present invention which can execute a method of the present invention, will now be described.

Referring now to FIG. 6 the apparatus shown includes a substrate station 20 on which can be mounted a substrate 10. Pins or similar means (not shown) can be provided on substrate station 20 by which to approximately align substrate 10 to a nominal position thereon. Substrate station 20 can include a vacuum chuck connected to a suitable vacuum source (not shown) to retain a substrate 14 without exerting too much pressure thereon, since substrate 14 is often made of glass. A flood station 68 is provided which can expose the entire surface of substrate 10, when positioned beneath station 68 as illustrated in broken lines in FIG. 4, to a fluid typically used in the in situ process, and to which all features must be exposed during each cycle (for example, oxidizer, deprotection agent, and wash buffer).

A dispensing head 210 is retained by a head retainer 208. The positioning system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head 210, by moving it in the direction of arrow 63, while transporter 100 is used to provide adjustment of the position of head retainer 208 (and hence head 210) in a direction of axis 204. In this manner, head 210 can be scanned line by line, by scanning along a line over substrate 10 in the direction of axis 204 using transporter 100, while line by line movement of substrate 10 in a direction of axis 63 is provided by transporter 60. Transporter 60 can also move substrate holder 20 to position substrate 10 beneath flood station 68 (as illustrated by the substrate 10 shown in broken lines in FIG. 4). Head 210 may also optionally be moved in a vertical direction 202, by another suitable transporter (not shown). It will be appreciated that other scanning configurations could be used. It will also be appreciated that both transporters 60 and 100, or either one of them, with suitable construction, could be used to perform the foregoing scanning of head 210 with respect to substrate 10. Thus, when the present application recites "positioning" one element (such as head 210) in relation to another element (such as one of the stations 20 or substrate 10) it will be understood that any required moving can be accomplished by moving either element or a combination of both of them. The head 210, the positioning system, and processor 140 together act as the deposition system of the apparatus. An encoder 30 communicates with processor 140 to provide data on the exact location of substrate station 20 (and hence substrate 10 if positioned correctly on substrate station 20), while encoder 34 provides data on the exact location of holder 208 (and hence head 210 if positioned correctly on holder 208). Any suitable encoder, such as an optical encoder, may be used which provides data on linear position.

Processor 140 also has access through a communication module 144 to a communication channel 180 to communicate with a remote station. Communication channel 180 may, for example, be a Wide Area Network ("WAN"), telephone network, satellite network, or any other suitable communication channel.

Head 210 may be of a type commonly used in an ink jet type of printer and may, for example, include five or more chambers (at least one for each of four nucleoside phosphoramidite monomers plus at least one for an activator solution) each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets). Application of a single electric pulse to an ejector will cause a droplet to be dispensed from a corresponding orifice. Certain elements of the head 210 can be adapted from parts of a commercially available thermal inkjet print head device available from Hewlett-Packard Co. as part no. HP51645A. Alternatively, multiple heads could be used instead of a single head 210, each being similar in construction to head 210 and being provided with respective transporters under control of processor 140 for independent movement. In this alternate configuration, each head may dispense a corresponding biomonomer (for example, one of four nucleoside phosphoramidites) or an activator solution.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The apparatus can deposit droplets to provide features which may have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m.

The apparatus further includes a display 310, speaker 314, and operator input device 312. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, and operation of display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required by the present invention, or any hardware or software combination which will perform those or equivalent steps.

The programming can be provided remotely to processor 141, or previously saved in a computer program product such as memory 141 or some other portable or fixed computer readable storage medium using any of those devices mentioned below in connection with memory 141. For example, a magnetic or optical disk 324a may carry the programming, and can be read by disk writer/reader 326.

A writing system which is under the control of processor 140, includes a writer in the form of a printer 150 which can write identifications onto substrate 10 by printing them in the form of the bar codes 356 (or alternatively on a housing carrying the substrate) each in association with a corresponding array 12 as shown in FIG. 1. Printer 150 may accomplish this task before or after formation of the array by the drop deposition system. The writing system further includes a data writer/reader 326 (such as an optical or magnetic disk drive) which can write data to a portable computer readable storage medium (such as an optical or magnetic disk). A cutter 152 is provided to cut substrate 10 into individual array units 15 each carrying a corresponding array 12 and bar code 356. An illumination source 170 can direct light through a beam splitter in the form of dichroic mirror 172 to illuminate substrate 10 on station 20 from below (the light shining through the back side 11b of substrate 10). An image capture system in the form of linescan camera 174 and processor 140, captures images through mirror 172 each of which simultaneously includes multiple target feature locations on substrate 10 following a cycle of droplet depositions at those locations. Processor 140 can extract from such captured images, the image set for each target feature location plus some predetermined region around that location (for example, a square surrounding that location) images each of which simultaneously includes multiple target feature locations following a cycle of droplet depositions at those locations. Camera 174 may have a pixel resolution of 30 $\mu$m or less, or 20 $\mu$m or less, and more preferably 10 $\mu$m or less. Any suitable camera may be used such as a CCD camera capturing a rectangular image, or a linescan camera. Processor 140 coordinates capture of the lines with the movement of substrate 10 during deposition of the reagent droplets.

Figure 7:
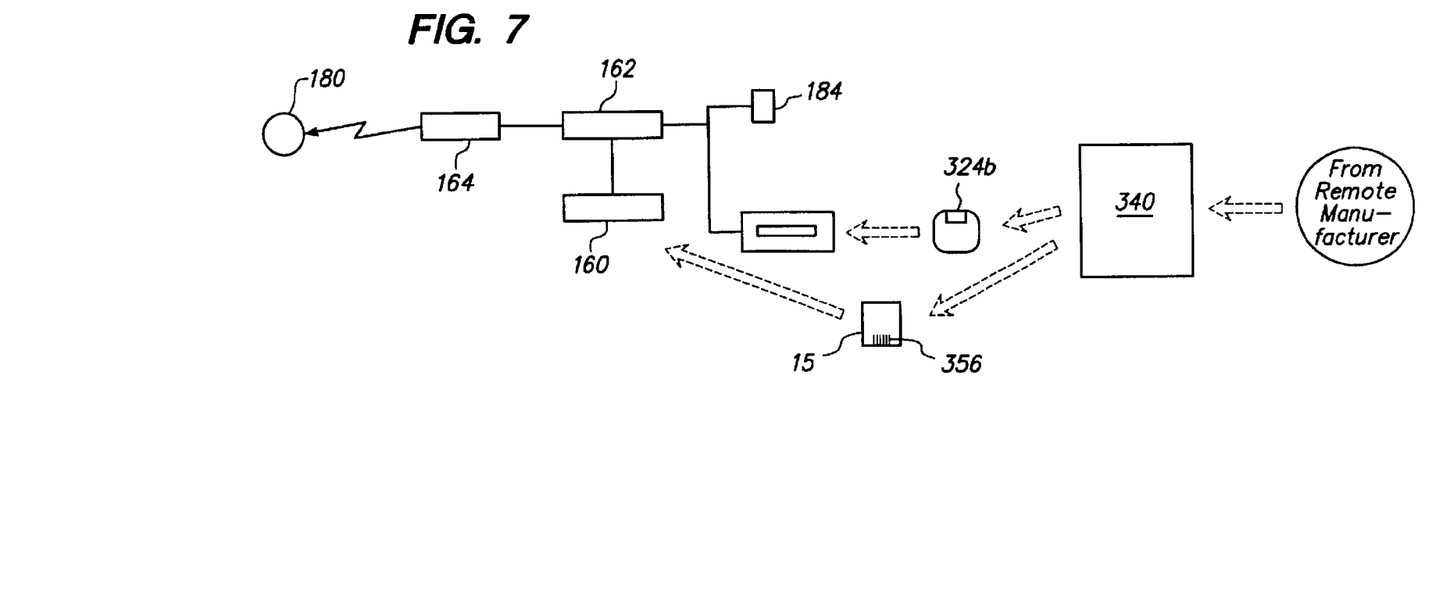
FIG. 7 is a schematic diagram of an apparatus at a user site which can execute a method of the present invention.

The above described components in FIG. 6 represent an apparatus for producing an addressable array, which is sometimes referenced herein as a "fabrication station". FIG. 7 illustrates an apparatus for receiving an addressable array, in particular a single "user station", which is remote from the fabrication station. The user station includes a processor 162, a memory 184, a scanner 160 which can interrogate an array, data writer/reader 186 (which may be capable of writing/reading to the same type of media as writer/reader 320), and a communication module 164 which also has access to communication channel 180. Memory 184 can be any type of memory such as those used for memory 141. Scanner 160 can be any suitable apparatus for interrogating an array, such as one which can read the location and intensity of fluorescence at each feature of an array following exposure to a fluorescently labeled sample. For example, such a scanner may be similar to the GENEARRAY scanner available from Hewlett-Packard, Palo Alto, Calif. Scanner 160 also includes though, a first bar code reader to read a each bar code 356 appearing on segment 15.

It will be understood that there may be multiple such user stations, each remote from the fabrication station and each other, in which case the fabrication station acts as a central fabrication station (that is, a fabrication station which services more than one remote user station at the same or different times). One or more such user stations may be in communication with the fabrication station at any given time. It will also be appreciated that processors 140 and 162 can be programmed from any computer readable medium carrying a suitable computer program. For example, such a medium can be any memory device such as those described in connection with memory 141, and may be read locally (such as by reader/writer 320 in the case of processor 140 or writer/reader 186 in the case of processor 162) or from a remote location through communication channel 180.

The operation of the fabrication station will now be described. It will be assumed that a substrate 10 on which arrays 12 are to be fabricated, is in position on station 20 and that processor 140 is programmed with the necessary layout information to fabricate target arrays 12. Processor 140 will generate a unique identification for each array 12 in the form of a corresponding bar code 356. Each identifier may be stored in memory 141 in association with the corresponding image sets for each feature of an array 12, or with composite overlays derived from those sets by processor 140 (as mentioned below).

Processor 140 controls fabrication, as described above, to generate the one or more arrays on substrate 10 by depositing for each target feature, multiple droplets of phosphoramidite reagents, and sends substrate 10 to flood station 68 for intervening or final steps as required, all in accordance with the conventional in situ polynucleotide array fabrication process described above. Preferably at each feature, during any one cycle multiple droplets of both the same phorsphoramidite solution and a tetrazole activator are deposited. For example, about five droplets of each may be deposited (making for a total of ten droplets in each cycle). Camera 174 captures images through mirror 172 each of which simultaneously includes multiple target feature locations on substrate 10 following a cycle of droplet depositions at those locations. The sub-set of droplets after which each image can be captured can equal this total number. However, it will be appreciated that this need not be the case (for example, ten total droplets may be deposited during a cycle, with an image being captured after each sub-set of five droplets, which two images are processed to determine total deposition area with a logical OR). Processor 140 extracts from such captured images, the image set for each target feature location plus some predetermined region around that location. At this point, if it is desired to provide feature characteristic information to an array user, processor 140 may store such image sets for all features of an array 12 into memory 141, or more preferably generates an overlay composite from all the sets (preferably by a logical AND operation as described above) and stores the overlay composites for all the features of an array 12 into memory 141. In either event, the image sets or overlay composites for an array 12 are stored in association with the corresponding unique identifier for that array. Note that the generation of an overlay composite can be performed after all images of a set are collected, or data processing can be performed as the images are obtained (that is, each image is processed as required immediately after it is obtained). Optionally, the overlay composites for an array or the image sets themselves, can later be stored onto a portable storage medium 324b in association with the corresponding array unique identification, by writer/reader 326 for provision to a remote user. Note that the overlay composites effectively represent a map of actual features on the array. It will be understood that the data form of the overlay composites can be varied though, such as being absolute data or relative data (such as relating the actual feature map to a corresponding target feature map forwarded from the fabrication station).

If it is not desired to provide overlay composites to an array user, but only to use the overlay composites as a quality control measure, then they can be used to reject an array 12 and direct it toward a garbage bin (not shown) if one or more predetermined number of features have one or more characteristics outside a predetermined tolerance. Such characteristics may include a minimum feature size (note that a feature size would be considered zero where the images indicate a complete failure to deposit a required phosphoramidite reagent during any one cycle). In an alternative, the deposition of additional droplets for a selected feature or droplets deposited at other features on the same or another array, can be based at least in part on an evaluated characteristic from an overlay composite for other droplets for that selected or other features. For example, if processor 140 generates logical AND for image sets of all features in an array and determines the resulting features have a characteristic outside a predetermined limit, such as a common mispositioning error, processor 140 may be able to compensate for this by repositioning head 210 during fabrication of other arrays. Other functions can be used, such as a logical "OR" where all of the area which has been covered by the various deposition cycles can be determined. The result of a logical "OR" shows the region where both full-length and non full-length polynucleotides are obtained (which can be helpful with, for example, HPLC analysis of DNA fragments)

It will be appreciated also, and any of the foregoing uses of the overlay composites can be combined. For example overlay composites can be both used to reject an array as described above, and the overlay composites or image sets still stored and forwarded to an end user for arrays that were not rejected. Furthermore, information from the image sets can be used for other purposes, such as monitoring variation in the size of a deposited droplet sub-set (which may indicate a problem).

Either before array fabrication on substrate 10 has been commenced, or after it has been completed, substrate 10 may be sent to writer 150 which, under control of processor 140, writes the unique bar codes 356 on substrate 10 each in association with its corresponding array (by being physically close to it in the manner shown in FIG. 1). The substrate 10 is then sent to a cutter 152 wherein portions of substrate 10 carrying an individual array 12 and its associated local identifier 356 are separated from the remainder of substrate 10, to provide multiple array units 15. The array unit 15 is placed in package 340 with storage medium 324b (if used) carrying overlay composites or image sets for the corresponding array 12, and the package then shipped to a remote user station.

The above sequence can be repeated at the fabrication station as desired for multiple substrates 10 in turn. As mentioned above, the fabrication station may act as a central fabrication station for each of multiple remote user stations, in the same manner as described above. Whether or not the fabrication station acts as a central fabrication station, it can optionally maintain a database of unique array identifiers in memory 141, each in association with the corresponding image sets or overlay composites.

At the user station of FIG. 7, the resulting package 340 is then received from the remote fabrication station. A sample, for example a test sample, is exposed to the array 12 on the array unit 15 received in package 340. Following hybridization and washing in a known manner, the array is then inserted into scanner 160 and interrogated by it to obtain interrogation results (such as information representing the fluorescence pattern on the array 12). The first reader in scanner 160 also reads the identifier 356 present on the array substrate 10 in association with the corresponding array 12. Using identifier 356, processor 162 may then obtain the corresponding overlay composites or image sets for array 12 from portable storage medium 324b or from the database of such information in memory 141 by communicating with that database through communication module 164 and communication channel 180. Alternatively, in the case where processor 162 has only obtained image sets, it can generate an overlay composite itself as needed.

Once processor 162 has obtained the overlay composites or image sets for an array 12, it can then control interrogation of the corresponding array by scanner 160 and/or the processing of the results of the interrogation, using such information. For example, an overlay composite may indicate a specific feature of such low quality (that is, having a characteristic outside a predetermined range) which is redundant with another feature, such that the scanner need not interrogate that specific feature for a given test, or alternatively that information read from that address can be ignored or deleted as useless. Following array interrogation, further processing of the interrogation results can be performed to evaluate the sample composition (such as for a specific target) based on the results of the interrogation. This further processing can be done by processor 162 or by a user examining the interrogation results. The interrogation results (raw data) or processed results from the interrogation results, could be forwarded (such as by communication) to a remote location for further evaluation and/or processing, or use, using communication channel 180 or reader/writer 186 and medium 190. This data may be transmitted by others as required to reach the remote location, or re-transmitted to elsewhere as desired.

In a variation of the above, it is possible that each array 12 and its substrate 10 may be contained with a suitable housing. Such a housing may include a closed chamber accessible through one or more ports normally closed by septa, which carries the substrate 10. It will also be appreciated that an image of a target feature location may include just a portion of that location, and that an image set preferably, but not necessarily, includes all of the droplets for that feature.

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of spots in FIG. 2 to include, for example, a series of curvilinear rows across the substrate surface(for example, a series of concentric circles or semi-circles of spots), and the like. Even irregular arrangements of the arrays or the regions within them can be used.

The present methods and apparatus may be used to deposit biopolymers or other moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be porous or non-porous, smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), Various further modifications to the particular embodiments described above are, of course, possible. Accordingly, the present invention is not limited to the particular embodiments described in detail above.

What is claimed is:

1. An apparatus for fabricating an array of features, comprising:
 a drop deposition system to deposit multiple reagent droplets for each of multiple target feature locations so as to form the array of features;
 an image capture system which provides a set of multiple images of a target feature location, each image of the set representing the target feature location following deposition of a corresponding subset of multiple droplets for that feature; and a processor which generates an overlay composite from the image set which comprises a region of overlap of the droplet sub-sets.

2. An apparatus according to claim 1 wherein the drop deposition system comprises a pulse-jet.

3. An apparatus according to claim 1 wherein the image capture system provides multiple image sets of respective multiple target feature locations, each image set representing a corresponding target feature location and in which each image represents the location following deposition of a corresponding sub-set of multiple droplets for that feature.

4. An apparatus according to claim 3 wherein the image capture system provides each set from multiple captured images each of which simultaneously includes multiple target feature locations following a cycle of droplet depositions at those locations.

5. An apparatus according to claim 1 wherein the drop deposition system alters the deposition of additional droplets for the feature, or of droplets for other features on the same or another array, based at least in part on the overlay composite.

6. An apparatus according to claim 1 additionally comprising a storage medium and a communication module, wherein the processor stores the overlay composite on the storage medium and causes the communication module to communicate the stored overlay composite to a remote user of the array.

* * * * *